United States Patent [19]

Evans et al.

[11] 4,414,983
[45] Nov. 15, 1983

[54] MEDICO-SURGICAL INSTRUMENTS

[75] Inventors: John M. Evans, Oxford; Keith Gilroy, Ashford, both of England

[73] Assignees: John M. Evans; Smiths Industries Public Limited Company, both of London, England

[21] Appl. No.: 294,126

[22] Filed: Aug. 19, 1981

[30] Foreign Application Priority Data

Sep. 12, 1980 [GB] United Kingdom ............... 8029617

[51] Int. Cl.³ .............................................. A61B 5/00
[52] U.S. Cl. .................................... 128/747; 128/748; 128/781
[58] Field of Search ...................... 128/200.21, 200.22, 128/207.28, 215, 218 A, 224, 747, 748, 763, 767, 128/781, 347, 214 F, 218 F, 218 PA, DIG. 12; 116/270; 604/131, 134, 135, 183, 184, 186, 207

[56] References Cited

U.S. PATENT DOCUMENTS

| | | | |
|---|---|---|---|
| 3,353,537 | 11/1967 | Knox et al. | 604/183 X |
| 3,709,211 | 1/1973 | Hawkins | 128/347 X |
| 3,785,367 | 1/1974 | Fortin et al. | 128/767 X |
| 3,943,917 | 3/1976 | Johansen | 128/763 |
| 3,957,051 | 5/1976 | Topham | 604/183 |
| 4,085,748 | 4/1978 | Boyer | 128/218 F X |
| 4,175,567 | 11/1979 | Patel | 128/748 |
| 4,215,699 | 8/1980 | Patel | 128/748 |

FOREIGN PATENT DOCUMENTS 2339407 8/1977 France ..................... 128/215

Primary Examiner—Kyle L. Howell
Assistant Examiner—Christine A. Fukushima
Attorney, Agent, or Firm—Pollock, Vande Sande & Priddy

[57] ABSTRACT

An instrument for detecting penetration of the epidural space comprises a barrel within which a plunger is urged forwardly by a resilient strap. The barrel has a nose on which a Tuohy needle is mounted. The inner surface of the barrel has a groove that extends along the barrel, being spaced from the nose. In operation the assembly is pushed forwardly until the tip of the needle contacts the spinal ligaments. The plunger is then pulled rearwardly past the end of the groove so that air enters the barrel and becomes trapped when the plunger is released and urged forwards by the strap. Penetration of the epidural space by the tip of the needle allows the trapped air to escape through the needle thereby providing an indication of penetration of the epidural space by causing the plunger to be moved forwards.

7 Claims, 7 Drawing Figures

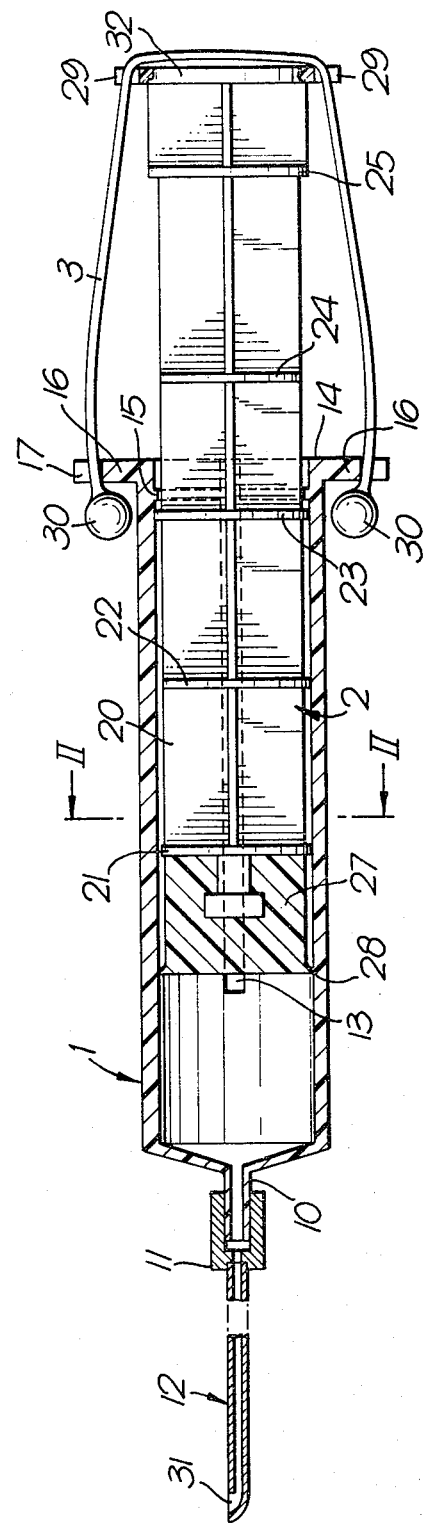

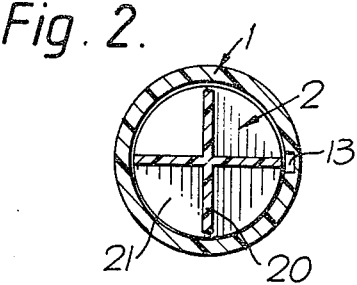
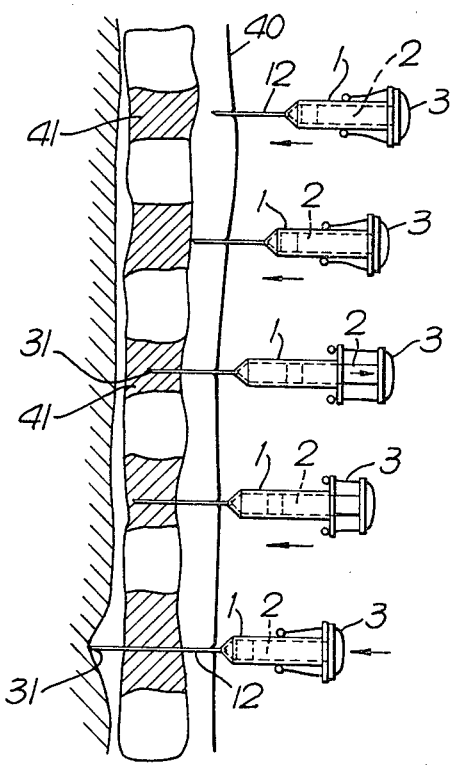

MEDICO-SURGICAL INSTRUMENTS

BACKGROUND OF THE INVENTION

This invention relates to medico-surgical instruments. The invention is, more particularly, concerned with instruments for use in detecting the epidural, or other body, space.

In epidural anaesthesia an anaesthetic drug is administered through a small-bore cannular or needle, one end of which is located within the patient's epidural space. The cannula is correctly positioned by means of a hollow-bore Tuohy needle that is pushed through the spinal ligaments into the epidural space, the cannula then being fed through the bore of the needle which is subsequently withdrawn to leave the cannula in place. In the past, difficulties have been experienced in correctly positioning the Tuohy needle. If the Tuohy needle is pushed too far it penetrates the matter underlying the epidural space and discomfort can be caused to the patient.

BRIEF SUMMARY OF THE INVENTION

It is an object of the present invention to provide an instrument that can be used to facilitate positioning of the Tuohy needle and reduce the risk of it being inserted too far.

According to one aspect of the present invention there is provided a medico-surgical instrument for use in inserting a hollow-bored needle into a body space, the instrument including a barrel member; a plunger moveable within said barrel member, the barrel member and the plunger together defining a cavity of variable volume that is arranged to open into the bore of said needle; and resilient means acting to urge said plunger and barrel member together so as to tend to reduce the volume of said cavity and thereby force fluid from said cavity through said bore when said needle penetrates said body space, the instrument being arranged to permit flow of fluid from outside said instrument into said cavity upon increasing the volume of said cavity.

The barrel member may be formed with passage means permitting flow of fluid from outside said instrument into said cavity when said cavity exceeds a predetermined volume.

According to another aspect of the present invention there is provided a medico-surgical instrument for use in inserting a hollow-bored needle into a body space, the instrument including a barrel member; a plunger moveable within said barrel member, the barrel member and the plunger together defining a cavity of variable volume that opens into the bore of said needle; resilient means acting to urge said plunger and barrel member together so as to tend to reduce the volume of said cavity and thereby force fluid in said cavity through said bore when said needle penetrates said body space; and passage means arranged to permit flow of fluid from outside said instrument into said cavity when said cavity exceeds a predetermined volume.

The passage means may include a groove formed along the inside of said barrel member, said groove being spaced from the end of the barrel member proximate said needle. Alternatively, said passage means may include an aperture formed through the wall of said barrel member and spaced from the end of the barrel member proximate said needle.

In use, fluid flow through the needle is prevented by contact of the spinal ligaments, or other body tissue, with the opening at the tip of the needle. The plunger and barrel are pulled away from one another to increase the volume of the cavity and permit entry of air. The resilient means then urges the plunger and barrel together trapping the air in the cavity. The plunger and barrel remain extended, because of the volume of trapped air, until the tip of the needle is unblocked on entry into the epidural, or other body, space. At this time, air is forced out of the tip of the needle by the resilient means, thereby causing relative movement of the plunger with respect to the barrel. By observing this movement the surgeon recognizes that the needle has entered the epidural, or other body, space.

An epidural space detector instrument, in accordance with the present invention, will now be described, by way of example, with reference to the accompanying drawings:

BRIEF DESCRIPTION OF DRAWINGS

FIG. 1 is a partially sectional side elevation, to an enlarged scale, of the instrument mounted on a Tuohy needle;

FIG. 2 is a cross-section of the instrument along the line II—II; and

FIGS. 3A to 3E illustrate, on a reduced scale, the instrument in use.

DETAILED DESCRIPTION

With reference to FIGS. 1 and 2, the epidural space detector instrument comprises a barrel 1 within which a plunger 2 is urged forwardly by a resilient strap 3.

The barrel 1 is of cylindrical shape and circular cross-section being about 8 cm long and 1.5 cm in diameter, although any alternative cross-sectional shape could be used. The barrel is made of a rigid polypropylene plastics material. A reduced-diameter nose portion 10 projects from the forward end of the barrel, the nose portion being inserted within the rear end 11 of a standard Tuohy needle 12. About 2 cm to the rear of the forward end of the barrel 1 the inner surface of the barrel is formed with a passage or groove 13 of rectangular section which extends rearwardly along the length of the barrel. Towards the rear end 14 of the barrel 1 there is formed an inwardly-directed lip 15 that prevents inadvertent withdrawal of the plunger 2 from the barrel. Two lugs 16 project radially outwards at the rear end 14, each lug being provided with a slot 17 for receiving opposite ends of the strap 3.

The plunger 2 is approximately 9 cm long having a plastics stem 20 of cruciform section. The stem 20 is provided with five radially reinforcing discs 21 to 25 spaced apart along the stem. The discs 21 to 25 are circular, the middle disc 23 and the rear disc 25 being of increased diameter. The middle disc 23 is located about 5 cm from the forward end of the plunger 2 and is arranged to limit withdrawal of the plunger, by engagement with the lip 15, to not more than about 2.5 cm. The rear disc 25 limits insertion of the plunger 2, by engagement with the rear end 14 of the barrel 1, so that the forward end of the plunger is prevented from contacting the forward end of the barrel 1. The forward disc 21 supports a sealing head 27 mounted at the forward end of the plunger 2. The head 27 is of a resilient elastomeric substance and is of a generally cylindrical shape being slightly smaller in diameter than the interior of the barrel 1. The forward end of the head 27 has a radial lip 28 that forms a seal about its circumference with the inner surface of the barrel wall. At the rear end of the plunger 2 there is provided a radially-extending finger grip 32 by which the plunger may be held and moved within the barrel 1. The grip 32 is formed with two slots 29 which receive the strap 3.

The strap 3 is of a resilient elastomeric material, such as thermoset rubber, and is about 4 cm long in its unstretched state. The ends of the strap 3 are formed into enlarged balls 30 which serve to prevent the strap being pulled from the slots 17 in the lugs 16. The resilience of the strap 3 is sufficient to urge the plunger 2 and barrel 1 together so that the plunger is forced to the forward end of the barrel against the action of any friction with the barrel.

In operation, the epidural space detector instrument is fitted to the rear end 11 of a Tuohy needle 12 and, with the plunger 2 in its normal position at the forward end of the barrel 1, the assembly is pushed forwardly so that the needle passes through the patient's skin 40 and underlying tissue, and into the spinal ligaments 41 (FIGS. 3A and 3B). The spinal ligaments are of a dense and gristly nature, the presence of which is readily apparent to the surgeon by the increased resistance to forward movement of the needle 12. In this position, the aperture 31 at the tip of the needle 12 is blocked by the surrounding spinal ligaments 41. The surgeon then pulls the plunger 2 rearwardly out of the barrel 1 (FIG. 3C) thereby further stretching the strap 3. As the surgeon begins to do this, the cavity formed between the plunger 2 and the barrel 1 increases in volume, but without initially permitting entry of fluid to the cavity, thereby forming a reduced pressure within the cavity that resists displacement of the plunger. The resistance is not, however, sufficient to prevent movement over a short distance and, as soon as the lip 28 of the plunger head 27 clears the forward end of the groove 13, air flows from outside the instrument, along the groove, between the plunger head and the wall of the barrel 1. In this way, pressure in the cavity is equalized with that outside the cavity. When this happens, the surgeon releases the plunger 2 so that it is urged forwards by the resilience of the strap 3 as far as the forward end of the groove 13 where the trapped air prevents further movement. The surgeon then continues pushing the assembly forwards (FIG. 3D) through the spinal ligaments 41. As soon as the aperture 31 at the tip of the needle 12 clears the spinal ligaments 41 the air trapped in the barrel 1 is forced by the resilience of the strap 3 through the bore of the needle 12 and out of its aperture 31. The plunger 1 therefore moves forwards rapidly (FIG. 3E) alerting the surgeon that the needle 12 is in the correct location. The epidural detector instrument is then removed, leaving the needle 12 in position. An epidural cannula (not shown) is subsequently pushed through the bore of the needle 12 in the normal way, after which the needle is removed by sliding rearwardly along the cannula.

It will be appreciated that the instrument could be used in applications other than for detecting the location of the epidural space. The instrument need not have a groove or grooves formed along the inner surface of the barrel, instead, apertures extending through the wall of the barrel could be used. Alternatively, the cylinder could have a bore that tapers, or is stepped to, a larger diameter to permit air passage around the plunger head when it is in a rearward position. The instrument could be provided with a one way valve that is arranged to allow air to enter the cavity from externally of the instrument when the plunger is pulled rearwardly, but to prevent air leaving the cavity on forward movement of the plunger, except through the bore of the attached Tuohy needle. The plunger could be urged forwardly by a helical spring or other resilient means.

What we claim is:

1. A medico-surgical instrument for inserting a hollow-bored needle into a body space, the instrument comprising: a barrel member; a needle having a bore therethrough; means mounting said needle on said barrel member; a plunger, said plunger being located for movement within said barrel member, the barrel member and the forward end of said plunger together defining a cavity of variable volume that opens into the bore of said needle; passage means in said barrel member, said passage means being spaced from the end of the barrel member proximate said needle, said plunger being movable between positions in which the forward end of the plunger is located rearwardly of said passage means so as to permit the flow of air from the outside of said instrument into said cavity, and in which the forward end of the plunger is located forwardly of said passage means such as to prevent the flow of air between the outside of said instrument and said cavity; and resilient means, said resilient means urging said plunger and said barrel member together so as to cause said plunger to move toward said needle to reduce the volume of said cavity and thereby force air from said cavity through said bore when said needle penetrates a body space, said plunger extending outwardly of the rearward end of said barrel member so that the movement of said plunger is visible from outside of said instrument so as to provide an indication of penetration of the body space by said needle.

2. A medico-surgical instrument according to claim 1, wherein said passage means includes a groove formed along the inside of said barrel member, the forward end of said groove being spaced from the end of the barrel member proximate said needle.

3. A medico-surgical instrument according to claim 1, wherein said resilient means includes a strap of elastic material that is stretched on increasing the volume of said cavity.

4. A medico-surgical instrument according to claim 3, wherein opposite ends of said strap are secured to said barrel member and wherein said strap is engaged intermediate its said ends by said plunger.

5. A medico-surgical instrument according to claim 1, wherein said needle is an epidural needle that is adapted for insertion into the epidural space through the spinal ligaments, the tip of said needle being blocked while being inserted through said spinal ligaments so that air is trapped in said cavity, and being opened on penetration of said epidural space so that air is forced out of said cavity causing displacement of said plunger relative to said barrel member and thereby giving an indication of penetration of said epidural space.

6. A medico-surgical instrument for inserting a hollow-bored needle into the epidural space, the instrument comprising a barrel member; a needle having a bore therethrough; means mounting said needle on said barrel member; a plunger, said plunger being located for movement within said barrel member, the barrel member and the plunger together defining a cavity of variable volume that opens into the bore of said needle, and a resilient strap urging said plunger into said barrel member so as to tend to reduce the volume of said cavity and thereby force fluid from said cavity through said bore when said needle penetrates said epidural space, the barrel member including a groove formed along its inside, said groove being spaced from the forward end of the barrel member proximate said needle such that air from outside the instrument can flow into said cavity via said groove when the plunger is located to the rear of the forward end of said groove.

7. A method of detecting penetration of a body space by a hollow-bored needle that opens at its tip, comprising the steps of:

(a) mounting the rear of said needle on a medico-surgical instrument comprising: a barrel member; a plunger, said plunger being located for movement within said barrel member, the barrel member and the plunger together defining a cavity of variable volume that opens into the bore of said needle; and resilient means, said resilient means urging said plunger and said barrel member together so as to tend to reduce the volume of said cavity and thereby force fluid in said cavity through said bore;

(b) pushing the tip of said needle into matter overlying said body space so that the tip of said needle is thereby blocked;

(c) moving said plunger and barrel member apart from one another against the action of said resilient means, thereby to increase the volume of said cavity and introduce fluid from outside said instrument into said cavity that is trapped and compressed in said cavity; and (d) pushing said needle through said matter until the tip of said needle penetrates said body space and is unblocked thereby allowing fluid to flow out of said cavity through said needle, permitting the plunger and barrel member to be moved together by the action of said resilient means and thereby providing an indication of the penetration of said body space.

* * * * *